United States Patent [19]

Salatino

[11] Patent Number: 5,085,084
[45] Date of Patent: Feb. 4, 1992

[54] METHOD AND APPARATUS FOR TESTING LEAD BONDS AND DETECTING FAILURE

[75] Inventor: Matthew M. Salatino, Satellite Beach, Fla.

[73] Assignee: Harris Corporation, Melbourne, Fla.

[21] Appl. No.: 615,358

[22] Filed: Nov. 19, 1990

[51] Int. Cl.[5] .............................................. G01N 3/08
[52] U.S. Cl. ..................................................... 73/827
[58] Field of Search .................. 73/827, 830, 837, 842, 73/834

[56] References Cited

U.S. PATENT DOCUMENTS

| 3,564,911 | 2/1971 | Slemmons et al. | 73/827 |
| 3,581,557 | 6/1971 | Drees et al. | 73/827 |
| 3,945,248 | 3/1976 | West | 73/827 |
| 4,282,759 | 8/1981 | Merrel | 73/827 |

OTHER PUBLICATIONS

Unger, "Self Test Ultrasonic Wire Bonding", Conference: 29th Electronic Components Conference, Cherry Hill NJ (14–16 May 1979).

*Primary Examiner*—Robert R. Raevis
*Attorney, Agent, or Firm*—Barnes & Thornburg

[57] ABSTRACT

A method includes applying a fluid force to a lead and determining if a lead separates at its bond in response to fluid force. The fluid can be applied to all the leads simultaneously or to given groups of leads. The determination of how many and which leads are separated is produced by positioning a sensor adjacent the leads and an indicator.

26 Claims, 3 Drawing Sheets

METHOD AND APPARATUS FOR TESTING LEAD BONDS AND DETECTING FAILURE

BACKGROUND AND SUMMARY OF THE INVENTION

The present invention relates to the testing of the bonding of leads connecting a device to a frame or support ring. The most prevalent method of interconnect from the bonding pads of an IC device utilizes individual wire bonding techniques. Either thermocompression, thermosonic, or ultrasonic bonding is used to connect the usual gold or aluminum wire to the interconnect pad (bonding pad) of the IC device. Typical wire diameters used are 0.001" to 0.003". High reliability requirements as well as process monitoring checks induced the development of wire pull machines to insure viable wire to pad or wire to lead connections.

This is typically done using a fine wire hook that is positioned around the interconnect wire to be tested and pulled in a vertical direction as shown in FIG. 1. The amount of force required to pull the wire from the pad is measured for a destructive test, or a fixed force is applied in a non-destructive mode. In this case if the bond does not lift, it is acceptable. Most space flight applications requires 100% non-destructive pull testing. Wire pull testing is performed under 25X–50X magnification and is typically a tedious task due to the very small spaces in which the hook must be maneuvered. Each wire must be individually pulled, which is time consuming, and can occasionally result in damage to the wire under test, or to surrounding wires.

With the advent of Tape Automated Bonding (TAB) in the high reliability environment, there is a need for an alternate method of non-destructive lead pull testing. TAB bonding entails attaching the entire series of leads, in this case flat, wide, previously patterned, to the device at one time. Typical attachment methods are thermocompression bonding, and recently developed thermosonic single point bonding. The TAB process allows the bonding pads on the device to be moved closer together, a feature desired by device designers to reduce device size as shown in FIG. 2. At the same time, the flat leads occupy more of the space in a plane radiating from the die surface than do the individual round wires of wire bonding.

This makes the task of pulling individual TAB leads very difficult due to the geometries involved. The hook typically used cannot easily fit between the leads and subsequently damages surrounding leads, making non-destructive testing very difficult. Other mechanical methods, such as pushing on the lead from the bottom surface have been attempted with limited success. Performing a destructive pull test is possible with the hook, proceeding around the device in one direction. When a lead is pulled away, clearance is made for the subsequent lead as illustrated in FIG. 1.

Thus it is an object of the present invention to provide a method and apparatus for testing bonding of leads which does not require a pull hook.

It is another object of the present invention to provide a method and apparatus for testing bonding of leads which is capable of being used with tape automated bonded leads.

It is an even further object of the present invention to provide a method and apparatus for testing bonding of leads in large groups or all simultaneously.

It is still an even further object of the present invention to provide a method and apparatus of identifying how many or which leads fail a bond test when more than one lead is tested simultaneously.

These and other objects are achieved by applying a fluid force to a lead and determining if a lead separates at its bond in response to fluid force. The fluid force is applied to the bonding face of the lead. Where the device includes a plurality of leads, the fluid can be applied to all the leads simultaneously or to given groups of leads. The determination of how many and which leads are separated is produced.

To determined which and how many leads are separated in response to the force, a sensor is positioned adjacent the leads and an indicator is connected to the sensor to indicate if one or more leads contact the sensor or which leads contact the sensor. The sensor can be a conductor connected in circuit with an indicator and the circuit is closed by a lead contacting the conductor. The fluid pressure applied may be for destructive testing, wherein the fluid pressure is increased until a lead separates from its bond. This pressure at which it separates is an indication of bond strength. Alternatively, non-destructive testing can be conducted, wherein the fluid pressure is applied at a pressure sufficient to separate unacceptably bonded leads while not separating acceptably bonded leads.

Other objects, advantages and novel features of the present invention will become apparent from the following detailed description of the invention when considered in conjunction with the accompanying drawings.

DETAILED DESCRIPTION OF THE DRAWINGS

Figure 1:
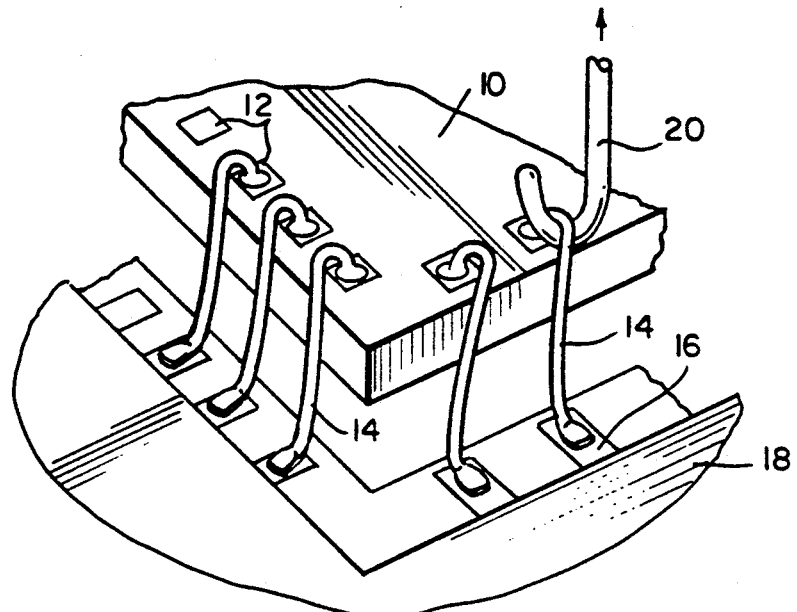
FIG. 1 is a perspective view of an integrated circuit connected to a lead frame by individual wire bonding techniques and a hook pulling procedure of the prior art.

FIG. 1 illustrates individual wire bonding wherein the integrated circuit or device 10 includes bonding pads 12. Wires 14 connect the IC device 10 from bonding pads 12 to leads or bonding area 16 of package 18. Hook 20 is used to apply the appropriate pull force. A tape automated bonding technique is illustrated in FIG.

Figure 2:
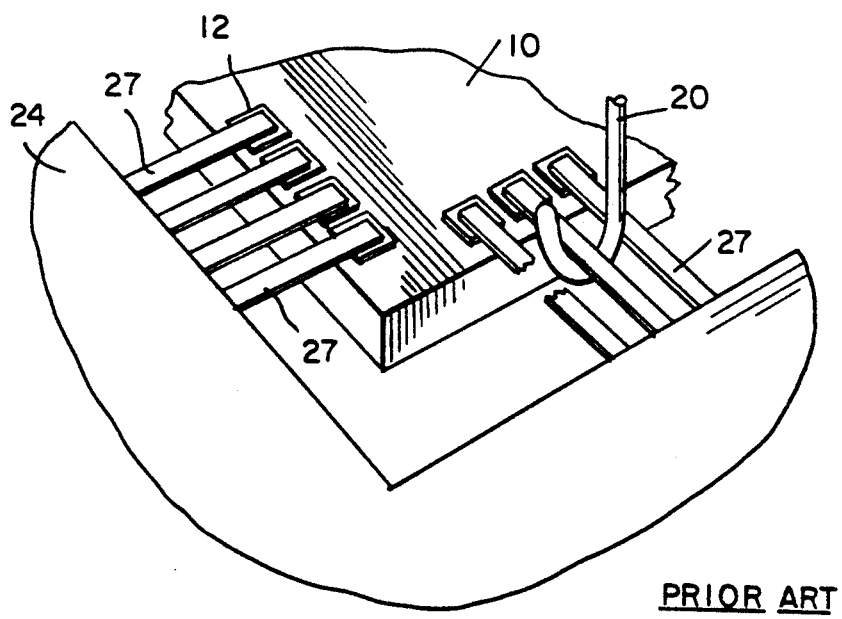
FIG. 2 is a perspective view of an integrated circuit connected to a lead frame using tape automatic bonding and a hook pulling procedure of the prior art.

2 wherein the IC device 10 including bonding pads 12 have connected thereto a plurality of tab leads 27 which are connected to the support ring or frame 24. The hook 20 in FIG. 2 also provides the pulling force to test the lead bonding.

Figure 3:
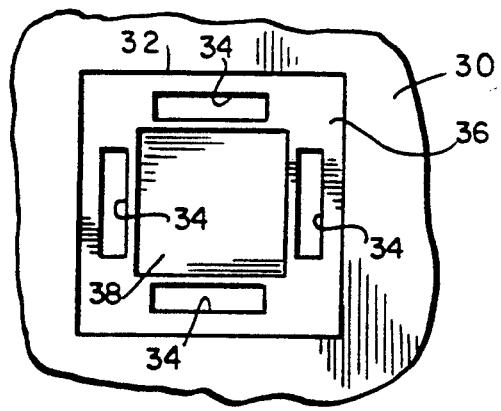
FIG. 3 is a plan view of the apparatus for applying the fluid pressure according to the principles of the present invention without the clamping structure.
Figure 4:
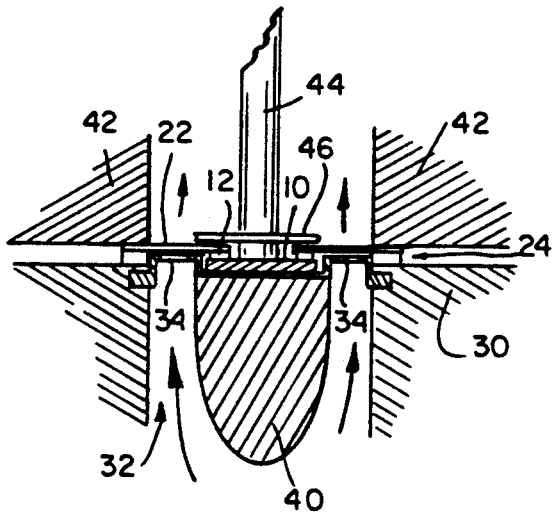
FIG. 4 is a side view of a device under test in the apparatus according to the principles of the present invention.

The test fixture of the present invention is illustrated in FIGS. 3 and 4 as including a base support structure 30 having a passage 32 and enclosed by cover 36. The cover 36 includes a recessed area 38 in the center to receive the device 10. Adjacent the recess 38 is a plurality of openings 34 to direct fluid against the leads from the passage 32. A cone 40 directs the fluid in passage 32 toward the openings 34. The device under test is secured to the support structure 30 by clamping elements 42 at the support ring 24. A support element 44 holds the device 10 in the recess 38 and includes a conductive plate 46 positioned above the leads adjacent to the bonding areas 12. Fluid pressure is applied to the passage 32 circulating up through openings 34 to apply force on the bottom surface which is common to the bonding surface of the leads 22.

One or more of the openings 34 may be closed such that a group of leads extending from one edge of the device 10 may be individually tested. Similarly, if desired portions of each of the openings 34 may be closed such that individual leads may be tested. Preferably groups of leads are tested simultaneously, one group at a time or all four groups simultaneously.

Figure 5:
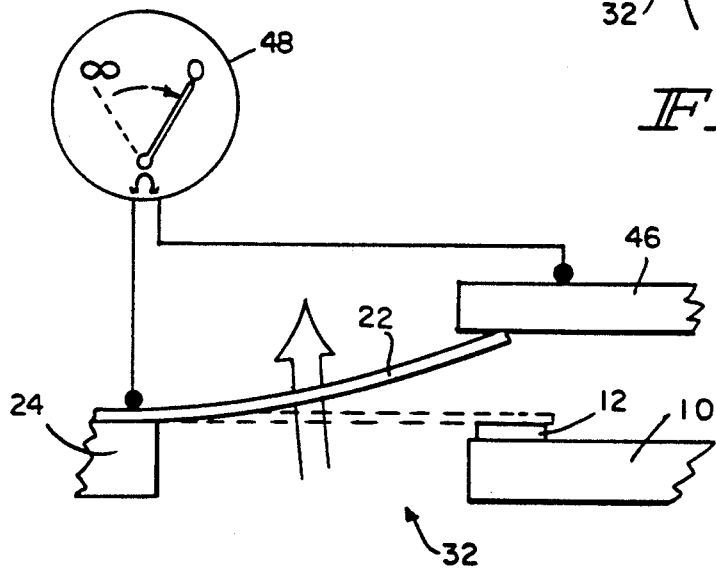
FIG. 5 is a schematic illustrating the measurement portion of the device under test.

As illustrated in FIG. 5, the conductive plate 46 is connected in a circuit with an indicator 48. An unacceptably bonded lead 22 completes the circuit by contacting the conductive plate 46. Indicator 48 would move from the infinite resistance or open circuit to a low resistance or closed circuit indication.

The fluid may either be a liquid or a gas and is focused on the leads. If a destructive test is to be conducted, the pressure of the fluid jet is progressively increased until one or more of the leads breaks its bond and comes into contact with the conductive plate 46. This pressure, after the breaking of the bond, is an indication of the strength of the bond. Alternatively, if non-destructive testing is required, an appropriate pressure is applied which is sufficient to move a lead 22 which is improperly bonded while not moving leads which are considered properly bonded.

If the testing is to indicate merely that one lead having an unacceptable bond will cause rejection of the device 10, the dropping of the resistance from an infinite to some close circuit resistance would be sufficient. If a given number of leads must contact plate 46 to indicate a acceptable device 10, different levels of resistance and sensitivity of indicator 48 must be used. Electrically, all the leads 22 are in parallel with each other and in series with the series resistance of the remainder of the circuit, including the plate 46 and the internal resistance of the indicator 48. Thus knowing the resistance of a lead 22, a value of four leads in parallel would be easily calculated and used as a threshold level for the appropriate resistance.

Figure 6:
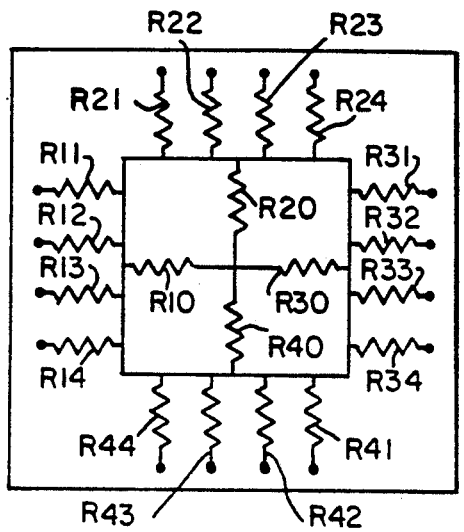
FIG. 6 is a schematic representation of a first embodiment of the conductive plate capable of individually indicating which lead has unacceptable bonds.

Alternatively, if knowing which leads specifically have failed is desired, appropriate resistance must be placed in series with the leads., As illustrated schematically in FIG. 6, the plate 46 would include a series resistor R10, R20, R30 and R40 representing each one of the groups of a plurality of leads at a given side of the device 10. Connected in series with the respective resistors R10, R20, R30 and R40 are the parallel resistors R11-R14, R21-R24, R31-R34 and R41-R44. The series connections of R10, R20, R30 and R40 with the parallel connections of R11-R14, R21-R24, R31-R34 and R41-R44 are in parallel with the other combinations of series and parallel combination resistors. By appropriately selecting the values of R10, R20, R30 and R40, the specific side of which a lead has failed can be identified. Similarly, the values of R11-R14 may be of different values and individually equal to the values of R21-R24, R31-R34 and R41-R44 respectively. This will provide an indication of which lead on each side has also failed. It should be noted that FIG. 6 is only an example of an appropriate circuit of series resistance on the plate 46 to produce the individual indication of which lead has failed.

Figure 7:
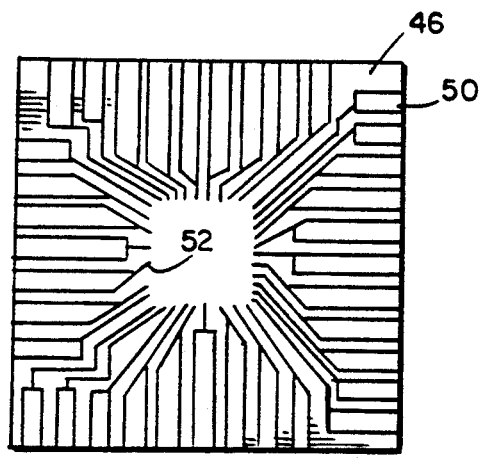
FIGS. 7 and 8 are the bottom and top sides respectively of a second embodiment of a conductive plate capable of indicating which lead has unacceptable bonds.
Figure 8:
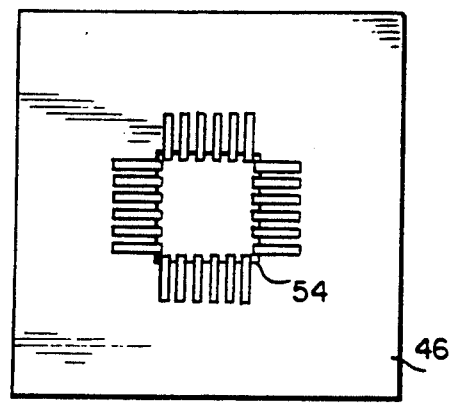

One way of implementing the schematic of FIG. 6 is shown in FIG. 7 wherein the conductive plate 46 is an insulative substrate having a plurality of conductive strips 50 thereon. The length of the strips would determine its resistivity. Leads 52 extending from the conductive resistive strips 50 would then be connected in the appropriate parallel and series circuits and connected to the appropriate indicator circuit. Alternatively, the conductive strips 50 and their leads 52 are connected to a encoder circuit 54 on the top side of the insulative strip 46 as illustrated in FIG. 8. The encode would sense which strip has completed a closed circuit and provide an encoded binary indicator to an indication circuit.

Figure 9:
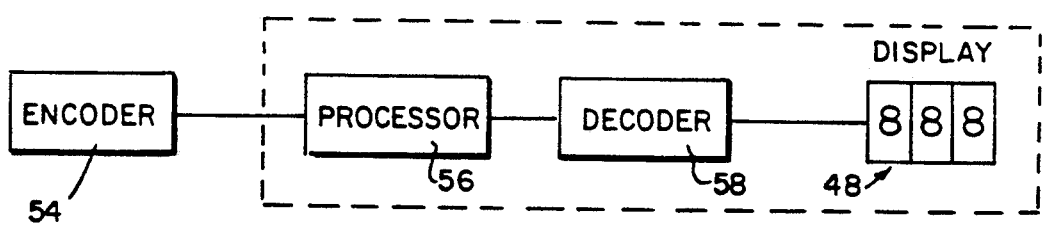
FIG. 9 is a block diagram of an encoder/decoder capable of illustrating which lead or leads has unacceptable bonds.

As illustrated in FIG. 9, the encoder 54 is connected to a processor 56 which communicates with the encoder 54 and provides the results to a decoder 58. The decoded signal is provided on display 48. The processor 56, decoder 58 and the display 48 may be part of a PC or other type of computer. The encoder 54 under the control of processor 56 may provide an indication of which individual or combination of individual leads have failed. This can be produced by any AND array encoder.

Although the present invention has been described and illustrated in detail, it is to be clearly understood that the same is by way of illustration and example only and is not to be taken by way of limitation. Although the fluidized pressure applied to the leads has been designed specifically for the closely positioned TAB bonded leads, it may also be applied to other lead configurations, including that of FIG. 1. Similarly, although tests have been performed on the leads connected to the device 10 and the support ring 24, the test may also be performed on the leads connected to a lead frame or other portions of the package if access is available to the bonding side of the leads. The spirit and scope of the present invention are to be limited only by the terms of the appended claims.

What is claimed:

1. A method of testing bonding of a plurality of leads connecting a device to a frame comprising:
    applying a fluid force directly to a bonding surface of a group of said leads greater than one simultaneously; and
    determining if any of said leads separates at their bonds in response to said fluid force.

2. A method according to claim 1 wherein said fluid is applied simultaneously to all of said leads.

3. A method according to claim 1 wherein determining determines which leads separate at their bonds in response to said fluid force.

4. A method according to claim 1 wherein determining determines how many leads separate at their bonds in response to said fluid force.

5. A method according to claim 1 wherein said device includes a plurality of groups of leads, each group extending from a different edge of said device; and said fluid is applied simultaneously to all leads of a group of leads, one group at a time.

6. A method according to claim 1 wherein said determining step includes positioning a sensor adjacent said leads, and indicating if a lead contacts said sensor.

7. A method according to claim 6 wherein said sensor includes a conductor connected in a circuit to an indicator and whose circuit is closed by a lead contacting said conductor.

8. A method according to claim 1 wherein said fluid is supplied at increasing pressure until a lead separates at its bond, the pressure at which said lead separates indicates bond strength.

9. A method according to claim 1 wherein said fluid is supplied at a pressure sufficient to separate unacceptably bonded leads while not separating acceptably bonded leads.

10. A tester of bonding of a plurality of leads connecting a device to frame comprising:
fluid means for applying fluid force directly to a bonding surface of a group of said leads greater than one simultaneously; and
determining means for determining if any of said leads separates at their bonds in response to said fluid force.

11. A tester according to claim 10 wherein said fluid means applies fluid simultaneously to all of said leads.

12. A tester according to claim 10 wherein said determining means determines which leads separate at their bonds in response to said fluid force.

13. A tester according to claim 10 wherein said determining means determines how many leads separate at their bonds in response to said fluid force.

14. A tester according to claim 10 wherein said device includes a plurality of groups of leads, each group extending from a different edge of said device; and said fluid means applies fluid simultaneously to all leads of a group of leads, one group at a time.

15. A tester according to claim 10 wherein said determining means includes a sensor means positioned adjacent said leads, and indicator means connected to said sensor means for indicating if a lead contacts said sensor means.

16. A tester according to claim 15 wherein said sensor means includes a conductor connected in a circuit to said indicator means and whose circuit is closed by a lead contacting said conductor.

17. A tester according to claim 10 wherein said fluid means supplies said fluid at increasing pressure until a lead separates at its bond, the pressure at which said lead separates indicates bond strength.

18. A tester according to claim 10 wherein said fluid means supplies said pressure at a pressure sufficient to separate unacceptably bonded leads while not separating acceptable bonded leads.

19. A method of detecting failure of the bonding of leads connecting a device to a frame comprising:
positioning a sensor adjacent said leads so as to be contacted by a failed lead;
applying a force to a lead independent of said sensor; and
indicating if a lead separates at its bonds in response to said force and subsequently contacts said sensor.

20. A method according to claim 19 wherein said sensor includes a conductor connected in a circuit to an indicator and whose circuit is closed by a lead contacting said conductor.

21. A method according to claim 19 wherein said indicating indicates which leads separate at their bonds in response to said force.

22. A method according to claim 19 wherein said sensor includes a conductor for each of said leads to be tested connected in a circuit to an indicator which indicates which leads have failed.

23. An indicator for indicating failure of bonding of leads connecting a device to frame which leads are subjected to force comprising:
a sensor means positioned adjacent said leads for sensing contact of said sensor means by a failed lead; and
indicator means connected to said sensor means for indicating if a lead separates at its bond in response to said force and subsequently contacts said sensor means.

24. An indicator according to claim 23 wherein said sensor means includes a conductor connected in a circuit to said indicator means and whose circuit is closed by a lead contacting said conductor.

25. An indicator according to claim 23 wherein said indicating means indicates which leads separate at their bonds in response to said force.

26. A method according to claim 23 wherein said sensor means includes a conductor for each of said leads to be tested connected in a circuit to said indicator means which indicates which leads have failed.

* * * * *